United States Patent
Hamill

(10) Patent No.: US 11,633,166 B2
(45) Date of Patent: Apr. 25, 2023

(54) SPATIAL REGISTRATION OF POSITRON EMISSION TOMOGRAPHY AND COMPUTED TOMOGRAPHY ACQUIRED DURING RESPIRATION

(71) Applicant: Siemens Medical Solutions USA, Inc., Malvern, PA (US)

(72) Inventor: James J. Hamill, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1085 days.

(21) Appl. No.: 15/268,909

(22) Filed: Sep. 19, 2016

(65) Prior Publication Data

US 2017/0079608 A1  Mar. 23, 2017

Related U.S. Application Data

(60) Provisional application No. 62/222,334, filed on Sep. 23, 2015.

(51) Int. Cl.
*A61B 6/00* (2006.01)
*A61B 5/08* (2006.01)
*A61B 6/03* (2006.01)

(52) U.S. Cl.
CPC .......... *A61B 6/5235* (2013.01); *A61B 5/0816* (2013.01); *A61B 6/032* (2013.01); *A61B 6/037* (2013.01); *A61B 6/4417* (2013.01); *A61B 6/5288* (2013.01); *A61B 2562/0261* (2013.01)

(58) Field of Classification Search
CPC ..... A61B 6/5235; A61B 5/0816; A61B 6/032; A61B 6/037; A61B 6/4417; A61B 6/5288; A61B 2562/0261
See application file for complete search history.

(56) References Cited

U.S. PATENT DOCUMENTS

| | | |
|---|---|---|
| 6,490,476 B1 | 12/2002 | Townsend et al. |
| 8,060,177 B2 | 11/2011 | Hamill |
| 2009/0116719 A1* | 5/2009 | Jaffray ............. A61B 6/5217 382/131 |
| 2013/0085375 A1 | 4/2013 | Hamill et al. |
| 2014/0133717 A1* | 5/2014 | Kabus ............. A61B 6/5264 382/128 |
| 2014/0328455 A1* | 11/2014 | Noshi ............. A61B 6/5235 378/20 |
| 2015/0221104 A1 | 8/2015 | Ra et al. |

OTHER PUBLICATIONS

Bettinardi et al., "Detection and compensation of organ/lesion motion using 4D-PET/CT respiratory gated acquisition techniques", Radiotherapy and Oncology. vol. 96, 2010. p. 311-316 (Year: 2010).*

(Continued)

*Primary Examiner* — Keith M Raymond
*Assistant Examiner* — Sean A Frith

(57) ABSTRACT

A method is disclosed for correcting the mismatch between computed tomography (CT) scan and positron emission tomography (PET) scan modalities caused by patient respiration by selecting PET image slices aligned with the phase and amplitude in which the CT was acquired PET image slices so they are aligned with the phase and amplitude in which the CT scan was acquired.

16 Claims, 13 Drawing Sheets

(56) References Cited

OTHER PUBLICATIONS

Nehmeh, et al. "Deep-Inspiration Breath-Hold PET/CT of the Thorax," The Journal of Nuclear Medicine. 48(1), 2007. p. 22-26 (Year: 2007).*
Schleyer, P., et al. "Retrospective data-driven respiratory gating for PET/CT," Phys. Med. Biology. vol. 54, 2009. p. 1935-1950 (Year: 2009).*
Didierlaurent, D., et al., "The retrospective binning method improves the consistency of phase binning in respiratory-gated PET/CT", Physics in Medicine and Biology. vol. 57, 2012. p. 7829-7841 (Year: 2012).*
Bailey, D., "3 Data Acquisition and Performance Characterization in PET", Positron Emission Tomography: Basic Science and Clinical Practice. Springer-Verlag London Ltd 2003. p. 69-90 (Year: 2003).*
Chang, Guoping et al., "Implementation of an Automated Respiratory Amplitude Gating Technique for PET/CT: Clinical Evaluation", The Journal of Nuclear Medicine, vol. 51, No. 1, Jan. 2010, pp. 16-24.

* cited by examiner

SPATIAL REGISTRATION OF POSITRON EMISSION TOMOGRAPHY AND COMPUTED TOMOGRAPHY ACQUIRED DURING RESPIRATION

CROSS-REFERENCE TO RELATED APPLICATION

This application claims priority under 35 U.S.C. § 119(e) to U.S. Provisional Application Ser. No. 62/222,334 filed Sep. 23, 2015, the contents of which are incorporated herein by reference.

FIELD

The present disclosure relates in general to a method for improved registration of computed tomography (CT) scan images and positron emission tomography (PET) scan images acquired in a PET/CT study, which provides improved correction of image registration for errors caused by patient respiratory movement during scanning.

BACKGROUND

CT scanning and PET scanning are well known methods for diagnostic medical imaging. CT scanning employs multiple X-ray images taken in multiple directions to generate a 3-dimensional image or multiple tomographic image "slices." PET scanning employs a gamma-emitting radiopharmaceutical ingested by a patient or injected into a patient. Multiple gamma ray images are taken in multiple directions to generate a 3-dimensional PET image or multiple slices. CT and PET scanning provide different information. For example, CT scanning generally has higher resolution and is superior for providing structural data such as the structure of bones, organs, etc. PET scanning generally has lower resolution but provides more useful information regarding the functional condition of body tissues and systems such as the cardiovascular system. PET is superior for indicating the presence of soft tissue tumors or decreased blood flow to certain organs or areas of the body, for example. The complementary strengths of CT and PET scanning can be provided simultaneously by performing both methods in a single apparatus and imaging session. However, combining CT and PET scanning presents technical challenges because CT and PET require different scan times and have different sensitivities to patient motion.

PET scanning requires a relatively long duration data acquisition period on the order of about 15 minutes for a typical clinically sufficient image. Typically, a large number of PET data acquisitions are acquired during this period. Also, during the PET scan, data in each slice are acquired at all respiratory phases, whereas, during a CT scan in a typical PET/CT study, such as a spiral CT scan, each CT image slice is acquired at a particular respiratory phase or amplitude because the CT scan is relatively fast. These differences result in a mismatch of the two modalities and limits the accuracy of the physician's interpretation of the scan.

Accordingly, there is a need in the art for improved methods for combined CT and PET scanning. It would be particularly beneficial to provide a method for combined CT and PET scanning that can correct for inaccuracies caused by patient motion such as motion caused by respiration.

SUMMARY

According to an aspect of the present disclosure, the mismatch of the CT and PET scan modalities is corrected by selecting PET image slices aligned with the phase and amplitude in which the CT was acquired.

In some embodiments, a method for matching a non-gated CT scan data, acquired during free breathing by a patient, to an emission scan, the method comprising the steps of:

(a) simultaneously recording the patient's respiratory waveform and performing a non-gated CT scan of the patient, wherein the recorded respiratory waveform represents a first respiratory waveform and the non-gated CT scan generating a set of axial slice CT images;

(b) simultaneously recording the patient's respiratory waveform and performing an emission scan of the patient, wherein the recorded respiratory waveform represents a second respiratory waveform and the emission scan generating a set of emission scan images;

(c) associating each of the axial slice CT images with a corresponding respiration phase interval or an amplitude interval on the first respiratory waveform, thus resulting in a plurality of CT scan-matched respiration phase intervals or amplitude intervals; and (d) matching each of the axial slice CT image to an emission scan image that is associated with the same respiration phase interval or amplitude interval as the corresponding CT scan-matched respiration phase interval or amplitude interval.

In some embodiments, the step (d) comprises:

identifying a plurality of respiration phase intervals or amplitude intervals on the second respiratory waveform that correspond to the plurality of CT scan-matched respiration phase intervals or amplitude intervals, thus resulting in a plurality of emission scan-matched respiration phase intervals or amplitude intervals; and identifying, among the set of emission scan images, those emission scan images corresponding to the plurality of emission scan-matched respiration phase intervals or amplitude intervals, thereby the emission scan images are matched to the attenuation and anatomy information in the axial slice CT images.

According to another aspect of the present disclosure a machine-readable storage medium is disclosed. The machine-readable storage medium tangibly embodies a program of instructions executable by a processor to cause the processor to perform operations for matching a non-gated computed tomography (CT) scan data, acquired during free breathing by a patient, to an emission scan, wherein the operations comprise the steps of:

(a) simultaneously recording the patient's respiratory waveform and performing a non-gated CT scan of the patient, wherein the recorded respiratory waveform represents a first respiratory waveform and the non-gated CT scan generating a set of axial slice CT images;

(b) simultaneously recording the patient's respiratory waveform and performing an emission scan of the patient, wherein the recorded respiratory waveform represents a second respiratory waveform and the emission scan generating a set of emission scan images;

(c) associating each of the axial slice CT images with a corresponding respiration phase interval or an amplitude interval on the first respiratory waveform, thus resulting in a plurality of CT scan-matched respiration phase intervals or amplitude intervals; and (d) matching each of the axial slice CT image to an emission scan image that is associated with the same respiration phase interval or amplitude interval as the corresponding CT scan-matched respiration phase interval or amplitude interval.

BRIEF DESCRIPTION OF THE DRAWINGS

The following will be apparent from elements of the figures, which are provided for illustrative purposes and are not necessarily to scale.

FIG. 6A is a non-gated PET image. FIG. 6B is an optimally gated (HD Chest) PET image. FIGS. 6C through 6J correspond to phase-based gating in gates 1 through 8.

DETAILED DESCRIPTION

Figure 1:
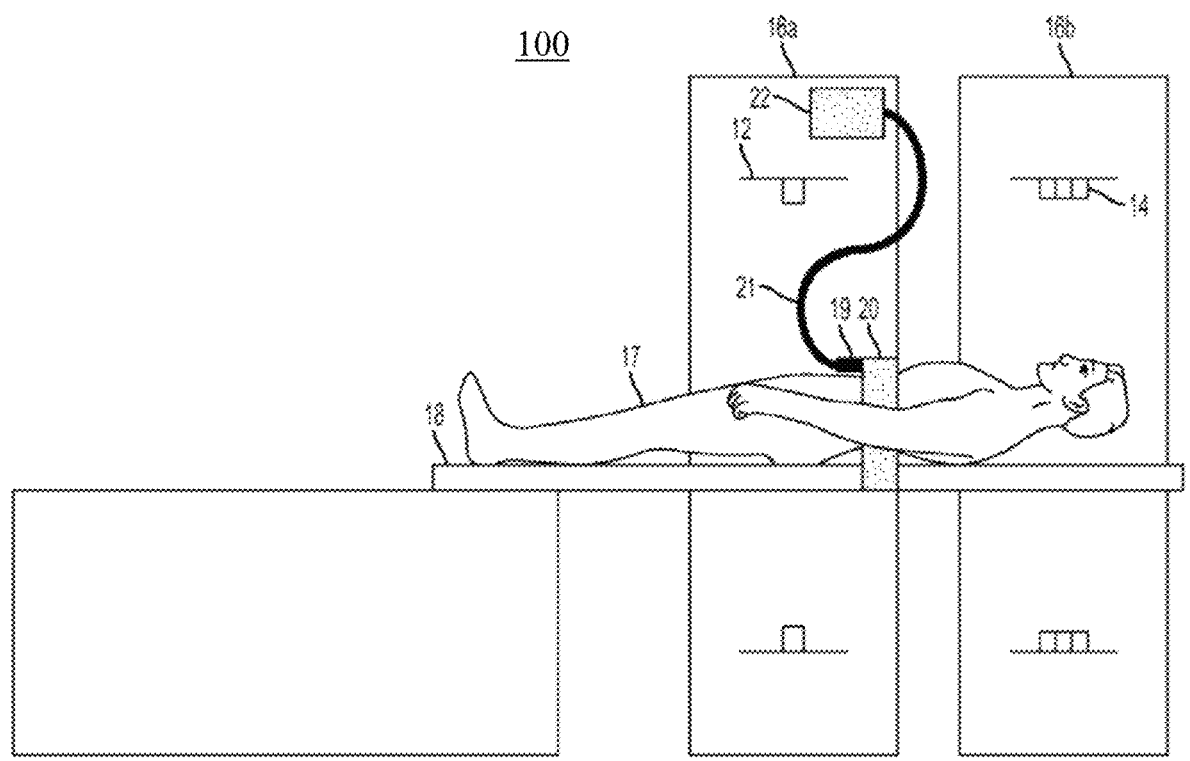
FIG. 1 illustrates an imaging device for sequentially performing CT and emission scanning, which can be used in accordance with the method of the present disclosure.

This description of the exemplary embodiments is intended to be read in connection with the accompanying drawings, which are to be considered part of the entire written description.

The nomenclature of the coordinate system in PET/CT scanning of a patient discussed herein is as follows: x=anatomically left to right with respect to the patient's body with increasing values further to the left; y=anatomically anterior to posterior, with increasing values toward the patient's posterior; z=anatomically inferior to superior with increasing values toward the patient's head.

PET/CT combines a PET scan (used to visualize and quantify physiology) with a CT scan (used to identify anatomical landmarks and pathology). Typically, the CT and PET scanners are in a single gantry and, typically, the PET and CT scans are performed a few minutes apart. The patient lies upon a bed that moves automatically between the CT scanner and the PET scanner. Commonly, a fast spiral CT scan is performed first. The bed moves across the patient z axis at a speed of several cm/s. This is followed by a PET scan that is performed in one of two ways: either step-and-shoot mode, with scans lasting 1 to 5 minutes at each of several bed positions along the z axis; or in continuous bed motion mode, with the scanner moving at a speed of approximately 1 mm/s.

Typically, in a 109-slice PET scanner the bed overlap parameter is 47 slices, meaning that the bed advances by 109−47=62 slices between bed positions. Since the slice thickness is 2 mm, this means that the bed advances 124 mm between bed positions.

PET/CT spatial alignment is likely to be imperfect because of patient motion between CT and PET. Even if the patient lies perfectly still, respiratory motion contributes to spatial misalignment. Free breathing normally occurs in these procedures. Human respiration is quite variable, with a combination of deep and shallow breaths occurring all the time. Since a period of 5 sec between breaths is common, although by no means universal, and since respiration affects the entire torso, and since 5 cm/s is a typical bed speed during spiral CT, one expects one or more breaths to occur during the CT portion of a PET/CT scan of the torso. A large number of breaths will occur during a PET measurement, perhaps as many as 20 or more.

Spatial alignment in PET/CT can be improved by quantifying the patient's breathing. This quantification is based on measuring something that moves with respiration, and using this measurement as a proxy for gating the CT or PET images so they are not three-dimensional functions of (X, Y, Z) but instead four-dimensional functions of (X, Y, Z, respiration). For example, the patient's chest elevation above the bed can be measured optically using an optical tracking device, or the tightness of a belt around the chest can be measured with a strain gauge provided in the belt. There are three common approaches to using the measurements. (1) Respiratory motions are neglected. This is the usual state of the art. We will say that a PET, a CT, or a PET/CT scan done this way is ungated. (2) The interval from one inspiration to the next is said to represent phases that range from 0 to 360 degrees. In one approach, the phases are said to increase linearly across the interval. PET or CT data can then be associated with phase intervals or bins. In the case of ten phase bins, 0 to 36 degrees represents bin 1, 36 to 72 degrees represents bin 2, etc. This approach is called phase-based gating. Motion-related differences between the two modalities can be reduced by applying the same gating criteria to PET and CT. (3) One records the respiration amplitude at each moment in time. The amplitude could be chest elevation or strain-gauge readout. PET or CT data can then be associated with amplitude intervals. This approach is called amplitude-based gating.

In some embodiments of the method, the recording of the respiratory waveform comprises using triggers. A trigger is a voltage level sent from the waveform recording system to the acquisition computers to mark a moment in time at which the respiratory phase reaches a particular phase, for example 0 degrees.

The principle of the present invention is that each z position in the CT image volume is uniquely associated with one amplitude or one phase, whereas each z position in a gated-PET image volume is associated with all possible amplitudes or phases. Thus, in the method of the present disclosure, CT images are matched to PET images at all z positions (i.e., positions along the z axis).

PET scanning is based on measuring the concentration of positron-emitting tracer at each point in a patient's body. The spatial coordinates are:

X represents a CT or PET X coordinate;
Y represents a CT or PET Y coordinate;
Z represents a CT or PET Z coordinate;
R(Z) represents a respiratory phase or amplitude bin in a CT image at a given Z position;
r represents a phase or amplitude bin in a gated PET sinogram or image;
s, phi, z, theta represent the four indices that specify all possible lines of response in an ungated PET sinogram as well recognized in the art;
an ungated PET sinogram is written $m_{ungated}$ (s, phi, z, theta); and
a respiratory gated PET sinogram is written $m_{gated}$ (s, phi, z, theta, r).

The present method associates a different amplitude or phase with each slice of the CT image. From the five-dimensional PET sinogram $m_{gated}$(s, phi, z, theta, r), create a four-dimensional PET sinogram $m_{ungated}$(s, phi, z, theta) by selecting a particular m at each slice (z). The rule is $m_{ungated}$(s, phi, z, theta)=$m_{gated}$(s, phi, z, theta, r(z)); the fifth index (the respiration coordinate, r) depends on the third one (the z axis position). From $m_{ungated}$(s, phi, z, theta), we reconstruct $PET_{matched}$(X, Y, Z) image. This method requires one image reconstruction for each phase range or amplitude range.

The present invention provides a method for matching or registering the PET and CT scan images acquired during free respiration. The registration compensates for the patient respiratory motion during PET scanning and allows more accurate matching of PET scan images to the CT scan images. The present method uses a respiratory waveform acquired during the CT scan while the patient is freely breathing and associates each axial CT slice with a particular phase or amplitude of the respiration. The PET reconstruction also uses waveform data and the image voxels from a given respiratory phase or amplitude are spatially rearranged so as to occupy the position at which the voxel was seen by the CT scanner.

The method disclosed in the present disclosure can be carried using a CT scanner and a PET scanner that can acquire image data in list mode. FIG. 1 shows one example of a combination PET/CT apparatus 100 that may be used with the method of the present disclosure. The CT scanner provides a three dimensional image of patient anatomy, which is used to estimate the attenuation of the annihilation radiation imaged by the PET scanner. The apparatus includes a CT scanner 16a (having detectors 12) and a PET scanner 16b (having detectors 14) in a common gantry (although not shown, it is appreciated that in other embodiments of the present invention, the CT scanner 16a and the PET scanner 16b can be in separate gantries). A patient 17 lies on a patient bed 18, that is movable between the CT scanner 16a and PET scanner 16b. In this example, the patient's respiration is monitored by a strain gauge 19 which is held against the patient's thorax with a belt 20. Electrical signals from the strain gauge 19 are communicated through a cable 21 to a data processing system 200 that is configured to, among other things, monitor the patient's respiration and measure the respiratory amplitude and generate respiratory waveform that shows both the respiratory amplitudes and phases.

Figure 2:
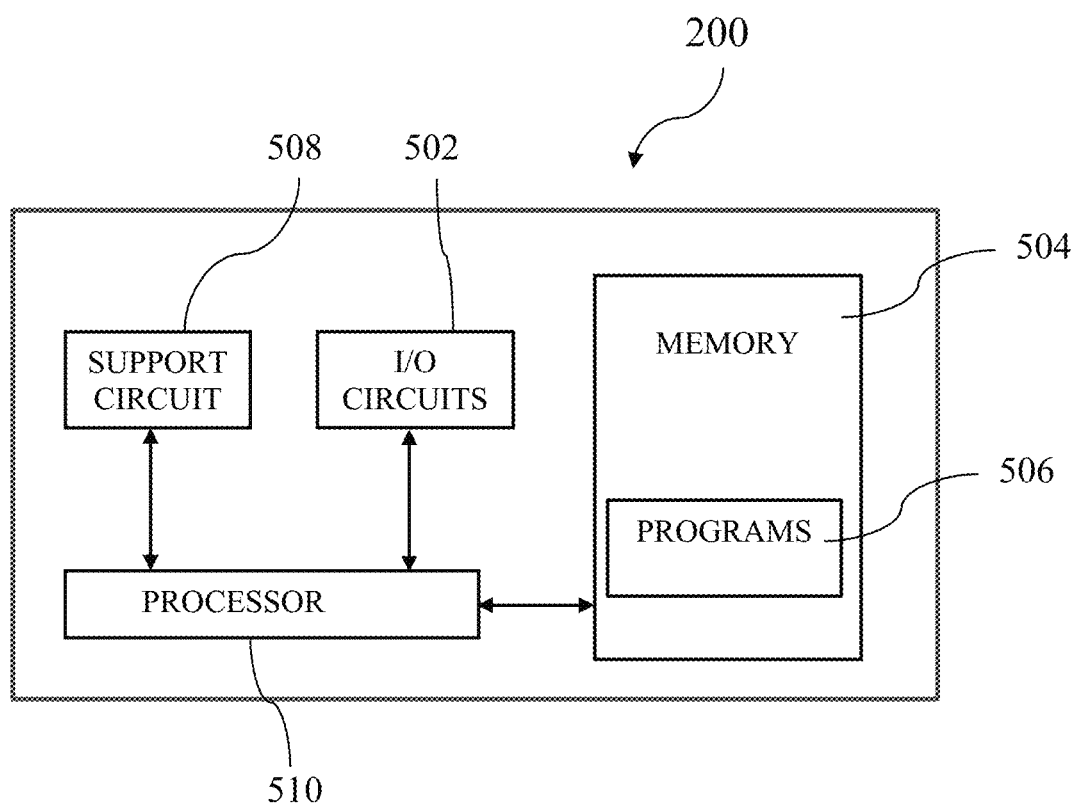
FIG. 2 illustrates an embodiment of a high-level block diagram of a general-purpose computer architecture 500 for providing phase matching in accordance with an embodiment of the present disclosure.

FIG. 2 shows the schematic block diagram of the data processing system 200 which includes a processor 510. The processor includes software that converts strain gauge signals into a respiratory waveform that quantitatively represents both the amplitude and phases (i.e., inspiration phase and expiration phase) of the patient's respiration cycle.

The data processing system 200 can be a general-purpose computer that includes the processor 510 as well as a memory 504 for storing control programs and the like. In various embodiments, the memory 504 also includes programs 506 (i.e. software routines) for performing the embodiments described herein. The processor 510 cooperates with conventional support circuitry 508 such as power supplies, clock circuits, cache memory and the like as well as circuits that assist in executing the programs 506 stored in the memory 504. As such, it is contemplated that some of the process steps discussed herein as software processes can be loaded from a storage device (e.g., an optical drive, floppy drive, disk drive, etc.) and implemented within the memory 504 and executed by the processor 510. Thus, various steps and methods of the present invention can be stored on a computer readable medium. The data processing system 200 also contains input-output circuitry 502 that forms an interface between the various functional elements communicating with the data processing system 200.

Although FIG. 2 depicts a general-purpose computer as the data processing system 200 that is programmed to perform various control functions in accordance with the present invention, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. In addition, although one general-purpose computer is depicted, that depiction is for brevity on. It is appreciated that each of the methods described herein can be utilized in separate computers.

In other embodiments, the respiratory amplitude can be measured by an instrument other than a strain gauge. For example, devices commonly used in radiation therapy use optical tracking devices such as digital cameras to optically track of the position of a marker placed on the patient's abdomen. Associated circuitry and computers in these devices supply a respiratory amplitude measurement which is communicated to the imaging system. Another example, commonly used in standalone magnetic resonance imaging scanner examinations (MRI), is a pneumatic device which generates an electronic signal corresponding to the air pressure in a flexible bladder held against the thorax and held tightly in place with a strap. The data processing system 200 is configured with software that generates respiratory waveform from the respiratory amplitude measurements.

In the following discussion of an example of the present inventive method, the emission scan is a PET scan.

The CT scanner 12 can be operated both normally and with triggering, and also can be configured to acquire a topogram. As per standard PET/CT imaging protocols, after the patient has received an appropriate dose of radiopharmaceutical (e.g., FDG), the patient is positioned on the patient bed 18, and an initial topogram is acquired. The topogram is used subsequently to define the examination range for the PET/CT image acquisition.

In accordance with one embodiment of the invention, after the acquisition of a topogram by the CT scanner, the operator reviews the topogram to determine and set the scanning positional limits for the diagnostic CT and PET scans. The PET/CT apparatus 100 is configured to perform the method for matching a non-gated CT scan data, acquired during free breathing by a patient, to an emission scan.

Figure 3:
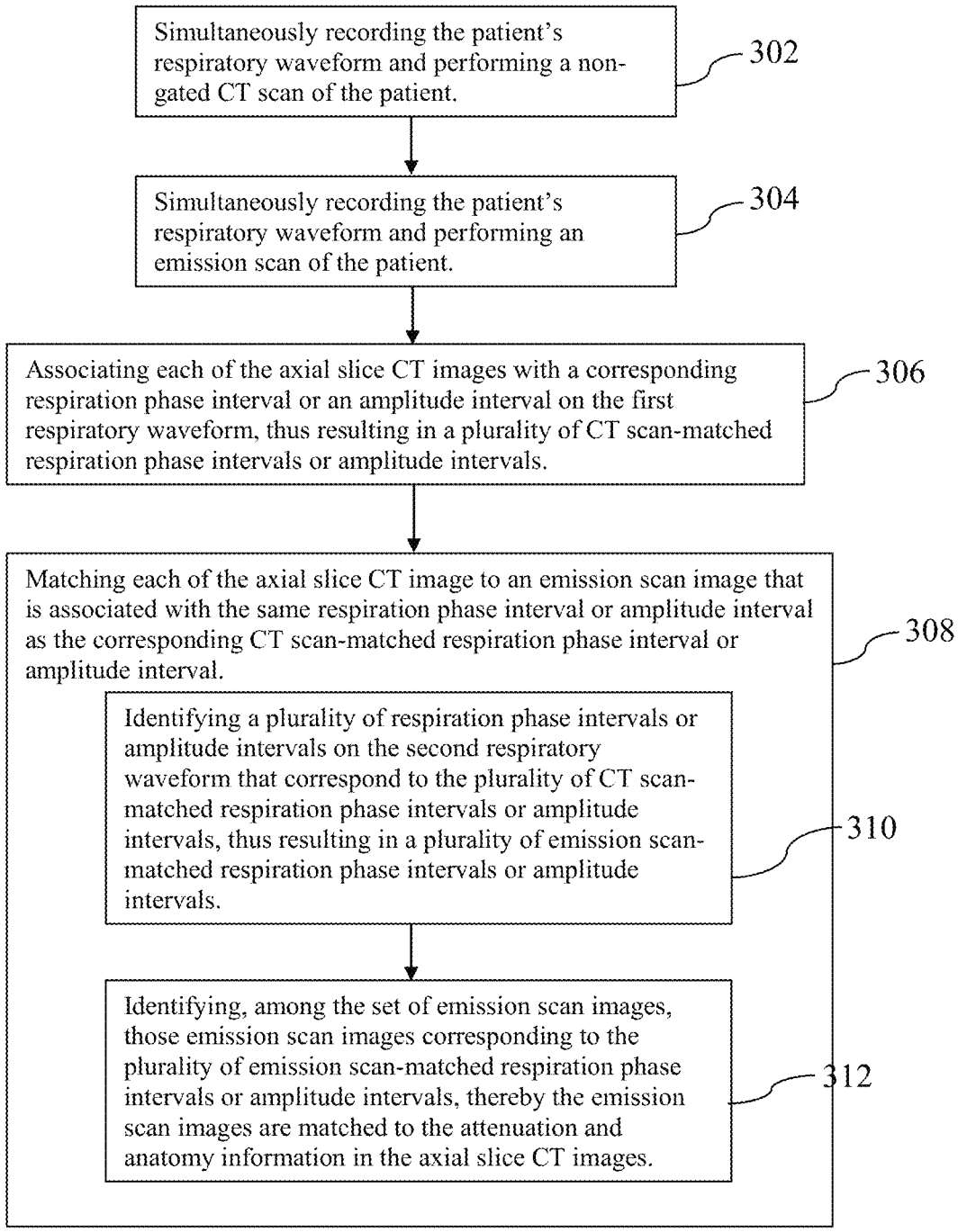
FIG. 3 is a flowchart illustrating the method of the present disclosure.

Referring to the flowchart 300 shown in FIG. 3, the method comprises the steps of: (a) simultaneously recording the patient's respiratory waveform and performing a non-gated CT scan of the patient, wherein the recorded respiratory waveform represents a first respiratory waveform and the non-gated CT scan generating a set of axial slice CT images. (See Box 302). During the CT scan, the patient follows a breathing pattern (e.g. free breathing) as instructed by the clinician. In some embodiments, the CT scan can be a spiral CT scan. The method further comprises, after the completion of the CT scan, (b) simultaneously recording the patient's respiratory waveform and performing an emission scan of the patient, wherein the recorded respiratory waveform represents a second respiratory waveform and the emission scan generating a set of emission scan images. (See Box 304). The inventor is not aware of any prior art method in which the patient's respiratory waveform is recorded as in the steps (a) and (b). The emission scan can be a PET scan conducted in list mode. The second respiratory waveform is correlated with the PET list mode data. Next, the method further includes, (c) associating or correlating each of the axial slice CT images with a corresponding respiration phase interval or amplitude interval on the first respiratory waveform, thus resulting in a plurality of CT scan-matched respiration phase intervals or amplitude intervals. (See Box 306). The method then includes, (d) matching each of the axial slice CT image to an emission scan image that is associated with the same respiration phase interval or amplitude interval as the corresponding CT scan-matched respiration phase interval or amplitude interval (See Box 308).

In some embodiments, the matching step (d) comprises: identifying a plurality of respiration phase intervals or amplitude intervals on the second respiratory waveform that correspond to the plurality of CT scan-matched respiration phase intervals or amplitude intervals, thus, resulting in a plurality of emission scan-matched respiration phases (See Box 310); and identifying, among the set of emission scan images, those emission scan images corresponding to the plurality of emission scan-matched respiration phase intervals or amplitude intervals, thereby the emission scan images are matched to the attenuation and anatomy information in the axial slice CT images (See Box 312).

In some embodiments of the method, the CT scan is spiral CT scan and the emission scan can be single-photon emission computed tomography (SPECT) scan. SPECT is a nuclear-medicine modality similar to PET, in which radiation from the patient are recorded by a gamma camera.

In some embodiments of the method, wherein the step (c) comprises associating each axial slice CT image with the respiration phase interval or amplitude interval, on the first respiratory waveform, that corresponds to the position z of the axial slice CT image.

In some embodiments of the method, wherein the step (d) comprises:

(e) forming gated PET sinograms (s, phi, z, theta, gate);
(f) reconstructing the gated PET sinograms to form images (x, y, z, gate); and
(g) at each axial slice, selecting the PET gate that matches the CT scan-matched respiration phase interval or amplitude interval acquired at position z in the CT scan, thereby forming images (x, y, z). Indices (s, phi, z, theta) represent commonly used coordinates that specify a line of response through the patient, connecting two detection crystals on opposite sides of the patient; s and phi are polar coordinates expressing the position of the line of response relative to the PET scanner's central axis, z expresses the line's position along that axis, and theta is the angle that the line forms relative to the central axis. The gate index is used to sort acquired information into various phases of respiration.

In some embodiments of the method, wherein the step (g) comprises: identifying a plurality of respiration phase intervals or amplitude intervals on the second respiratory waveform that correspond to the plurality of CT scan-matched respiration phase intervals or amplitude intervals, thus resulting in a plurality of PET scan-matched respiration phases; and identifying, among the set of PET scan images, those PET scan images corresponding to the plurality of PET scan-matched respiration phase intervals or amplitude intervals, thereby the PET scan images are matched to the attenuation and anatomy information in the axial slice CT images.

In some embodiments of the method, wherein the step (d) is based on:

(h) forming one PET sinogram (s, phi, z, theta) that selects PET data that matches the CT scan-matched respiration phase acquired at position z in the CT scan; and
(i) reconstructing the PET sinogram to form images (x, y, z).

In some embodiments of the method, wherein the step (h) comprises: identifying a plurality of respiration phase intervals or amplitude intervals on the second respiratory waveform that correspond to the plurality of CT scan-matched respiration phase intervals or amplitude intervals, thus resulting in a plurality of PET scan-matched respiration phase intervals or amplitude intervals; and identifying, among the set of PET scan images, those PET scan images corresponding to the plurality of PET scan-matched respiration phase intervals or amplitude intervals, thereby the PET scan images are matched to the attenuation and anatomy information in the axial slice CT images.

According to another aspect of the present disclosure a machine-readable storage medium, such as the memory 504 of the data processing system 200 is disclosed. The machine-readable storage medium tangibly embodies a program of instructions executable by a processor, such as the processor 510, to cause the processor to perform operations for matching a non-gated computed tomography (CT) scan data, acquired during free breathing by a patient, to an emission scan, wherein the operations comprise the steps of the method illustrated in the flow chart 300 of FIG. 3 discussed above.

EXPERIMENTAL

Figure 4:
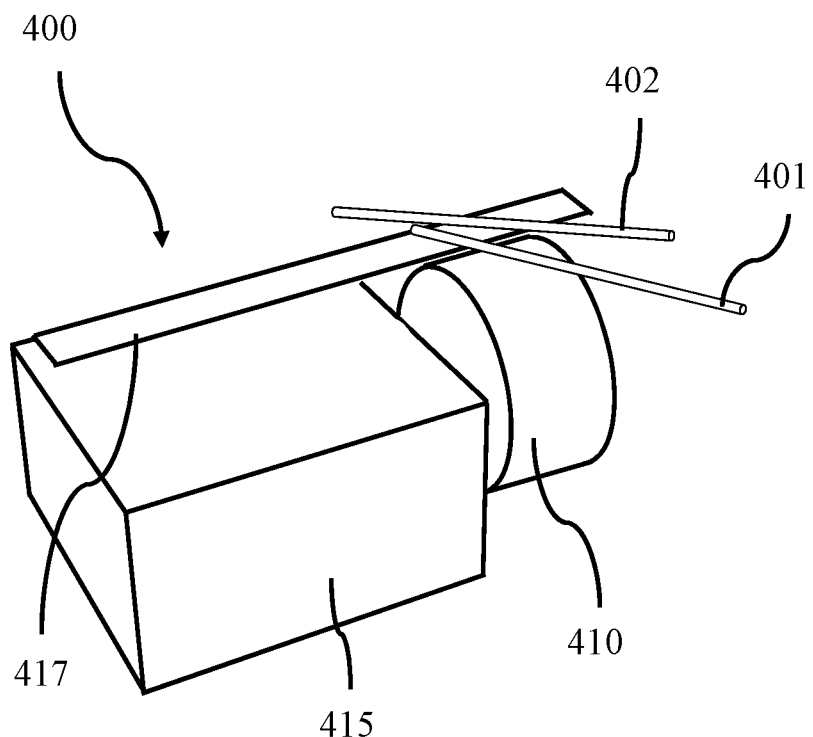
FIG. 4 is a photograph of a two-line-source phantom used in the experimental set up discussed in the present disclosure.

PHANTOM DEMONSTRATION OF RESPIRATORY PHASE MATCHING IN PET/CT SCAN: Referring to FIG. 4, inventor performed an experiment to demonstrate the respiratory phase matching method according to an embodiment of the present disclosure. Two metal line sources 401 and 402 containing Ge-68 radioactivity were attached to a phantom with two line sources 400, one of which moved in a respiration-like pattern and one of which did not move. The metal was expected to be seen in a CT scan, and the radioactivity was expected to be seen in a PET scan. One line source 401 was attached to the phantom's moving barrel 410 to simulate a moving body portions of a patient during respiration. The second line source 402 was affixed to a non-moving part, the main body 415 of the Anzai phantom 400 to simulate a non-moving body portion and as a reference. In order to position the second line source 402 near the first line source 401, the second line source 402 was affixed to a ruler 417 which was then affixed to the main body 415 of the two-line-source phantom. A strain gauge was placed at the back side of the phantom, where it would respond to motion by creating a waveform similar to what is seen in human respiration, which would be recorded by a digital computer such as the data processing system 200.

Since PET/CT requires a CT scan and a PET scan, we first scanned the phantom with a CT scanner to generate a topogram to determine the range for the PET scan. Then, a CT scan, also referred to as the fast or high-pitch scan, was conducted at 120 kV, 5 mm slice, 64×0.6 mm, recon increment 5 mm, pitch 1.4, 0.5 s rotation, in craniocaudal scan direction while the strain gauge recorded the waveform of the phantom's moving barrel simulating a patient's respiratory waveform. It is to this CT scan, or one like it, that the invention will match the PET scan whose acquisition is now described.

Next, a PET scan was conducted in a 2 minute list-mode acquisition. Next, a second CT scan, also referred to as the slow or low-pitch scan, was conducted with the same parameters as the first CT scan except that the pitch was 0.4. The invention applies equally to the fast CT scan and to this slow CT scan. This fact is illustrated by showing results from both.

Figure 5A:
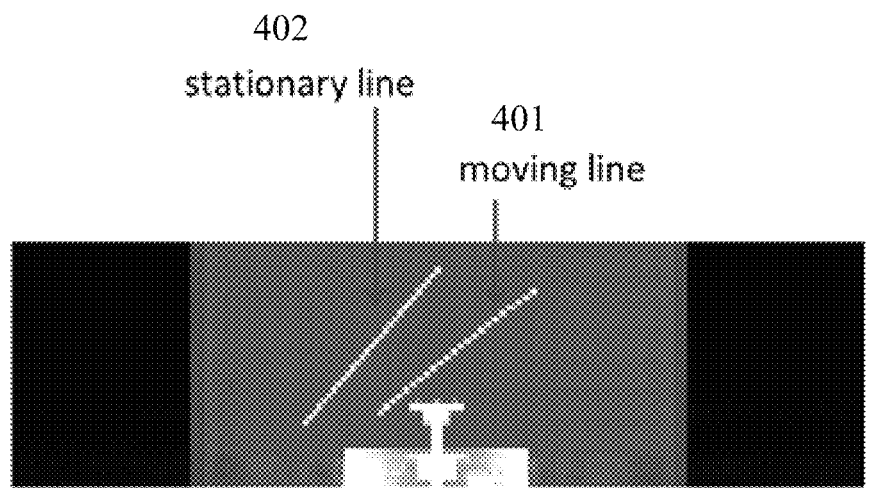
FIG. 5A shows the CT image of the two-line-source experiment in the high-pitch CT scan.
Figure 5B:
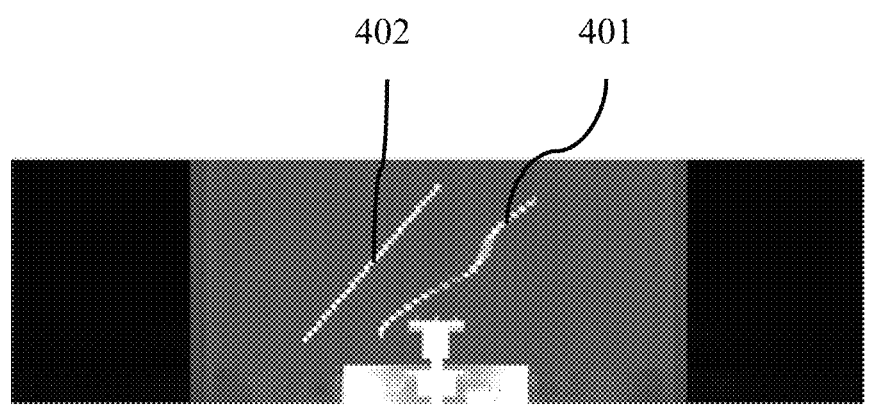
FIG. 5B shows the CT image of the two-line-source experiment in the low-pitch CT scan.
Figure 6A:
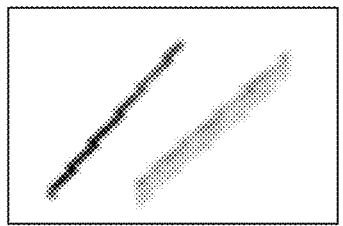
FIGS. 6A-6J show PET images with different replay parameters.
Figure 6B:
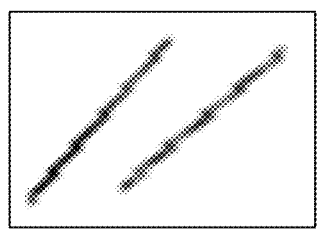
Figure 6C:
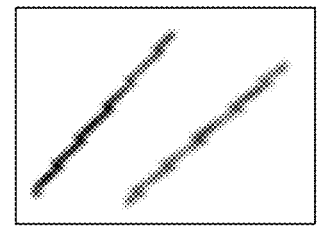
Figure 6D:
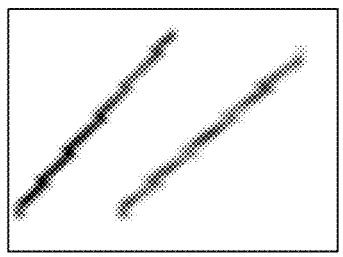
Figure 6E:
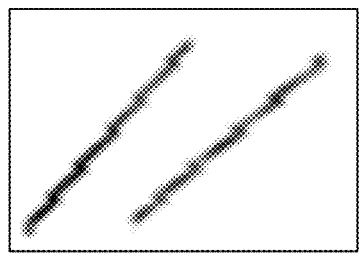
Figure 6F:
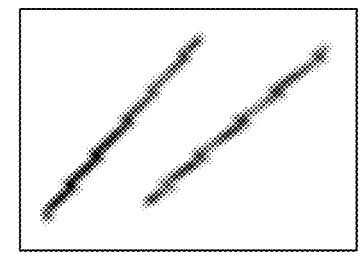
Figure 6G:
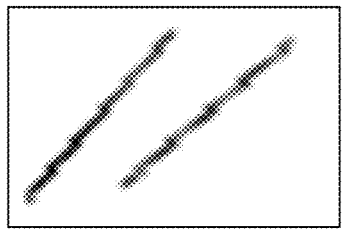
Figure 6H:
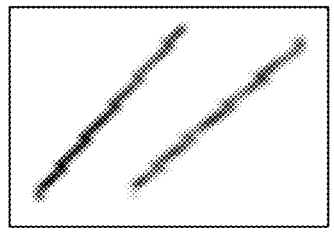
Figure 6I:
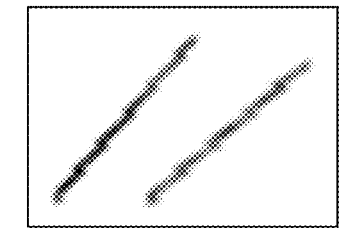
Figure 6J:

OVERVIEW OF THE RECONSTRUCTED CT AND PET IMAGES: FIGS. 5A and 5B show maximum intensity projection (MIP) CT images from the measurement. Whereas both lines were actually straight, the image of the moving line was greatly distorted in the low-pitch scan shown in FIG. 5B. The CT image of the moving line in the high-pitch scan shown in FIG. 5A was also distorted, though this was not so easily noticed. The image of the stationary line was straight in both scan images.

FIGS. 6A-6J show PET images with different replay parameters. Because the static image in FIG. 6A used all events, the moving line appeared to be blurred whereas the stationary one was comparatively sharp. The optimally gated image (HD Chest) in FIG. 6B used the best 35% of the events. In that image, the moving and stationary lines had similar sharpness. Phase-based gating scan images shown in FIGS. 6C through 6J also resulted in similar sharpness for the two lines. In every case, the line images were straight. There was no distortion as in CT.

Figure 7:
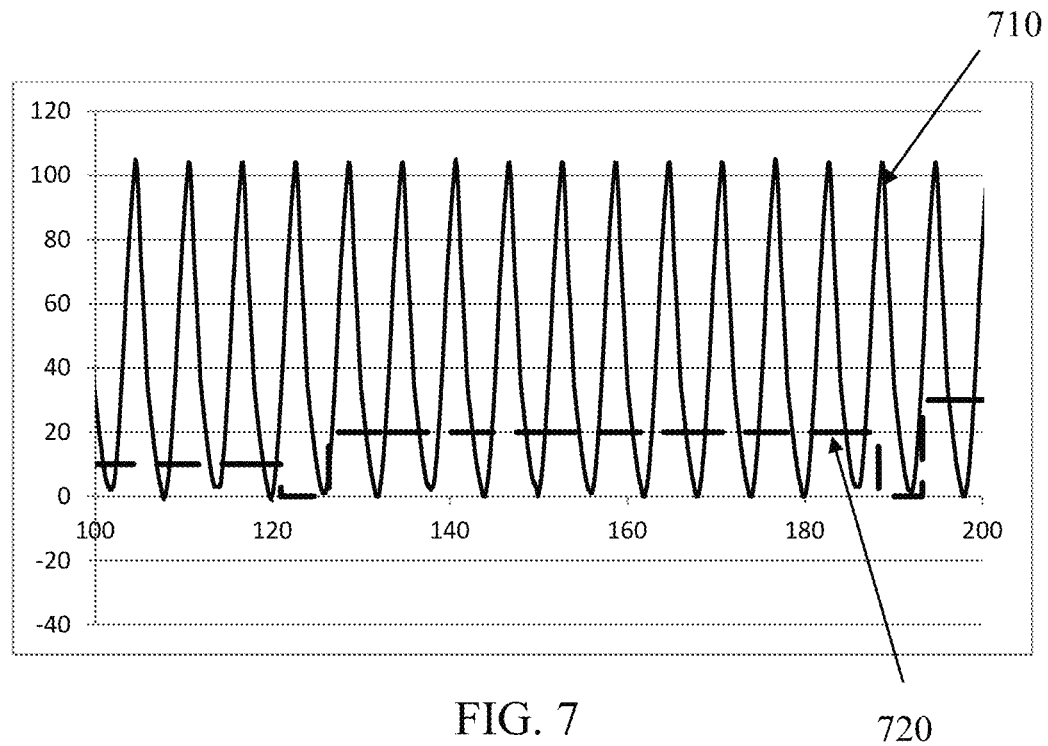
FIG. 7 illustrates waveform and beam-on signals from a waveform file, corresponding to acquisition of the topogram and the first CT scan. The horizontal axis represents time in seconds.
Figure 8:
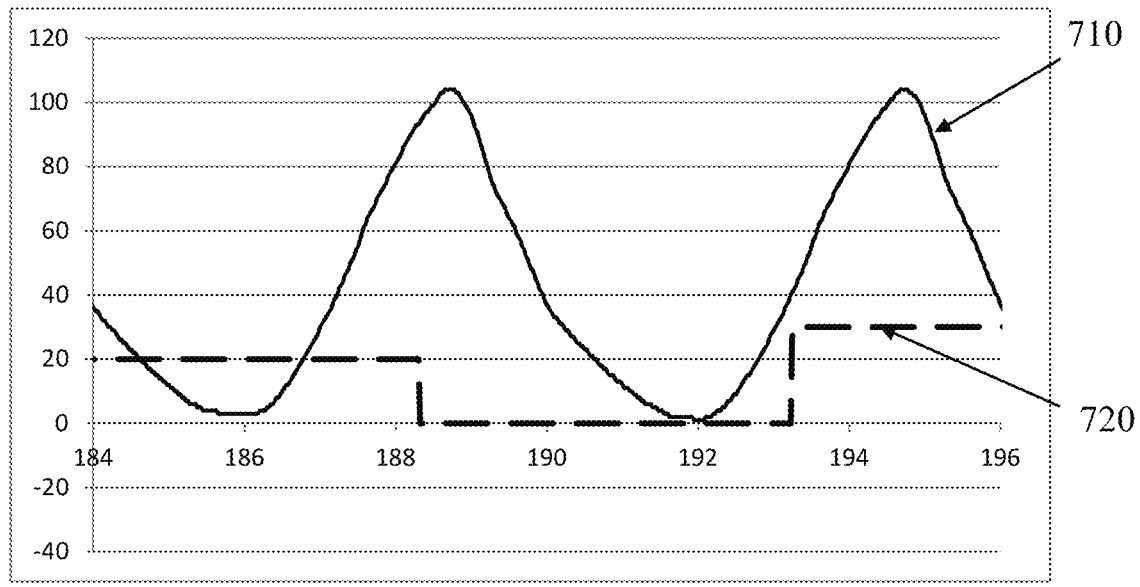
FIG. 8 shows a zoomed in portion of the plots shown in FIG. 7.

DETERMINING TIME AND RESPIRATORY PHASE IN THE CT SCAN AND MATCHING THE CT IMAGES TO THE PET IMAGES: The process of determining time and respiratory phase in the CT scan and matching the CT images to the PET images will be described two times, once for the high-pitch scan and once for the low-pitch scan. The waveform signal 710 and beam-on signal 720 from the high-pitch CT scan are shown by FIG. 7, representing the full measurement. FIG. 8 is a zoomed in view of the waveform of FIG. 7 showing the time during which the CT scan was acquired. The dip in the beam-on signal 720 120 seconds into the waveform measurement corresponds to the acquisition of the topogram. The second dip at 190 seconds corresponds to the fast CT scan. This shows that, during the fast CT scan, the phantom moved through less than one cycle of simulated respiration.

Figure 9:
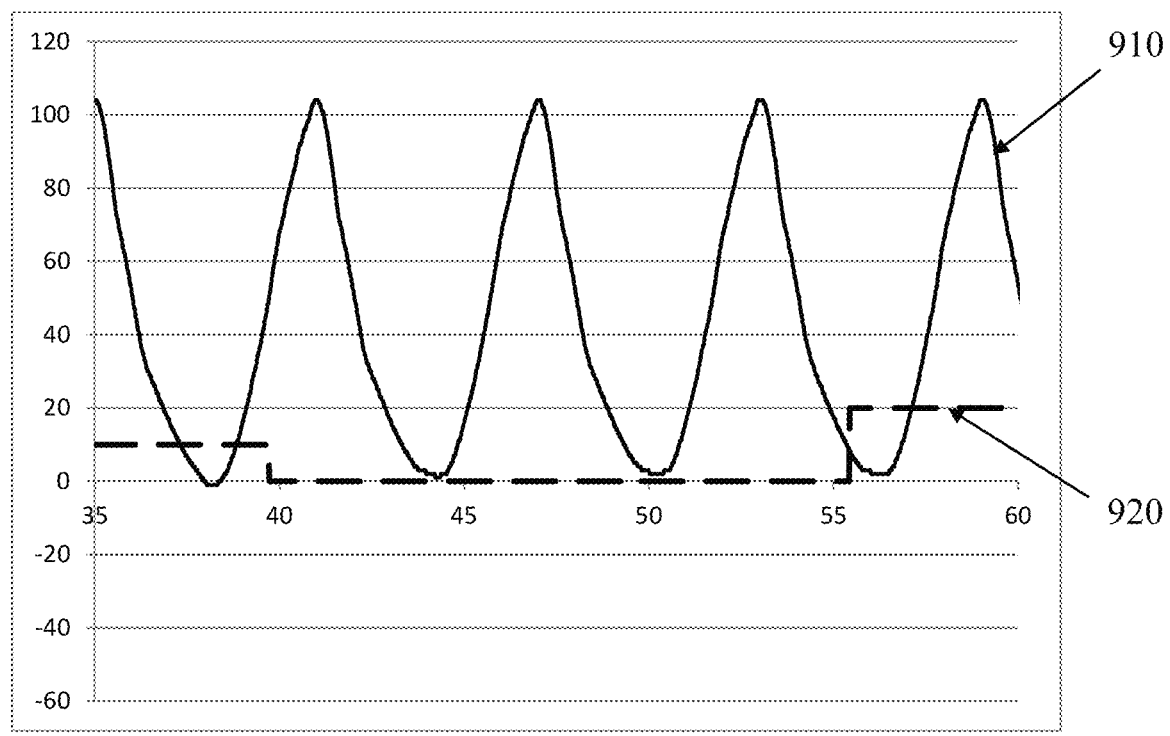
FIG. 9 plots the respiration-like waveform.

Plots of the waveform signal 910 and the beam-on signal 920 from the low-pitch CT scan data are shown in FIG. 9. There were two and a half cycles of simulated respiratory motion during the scan. Inspecting waveform data that had been written to a digital computer file, inventor determined the start and stop times relative to the start of each file, and the total beam-on time in the two scans. The results are shown in Table 1.

TABLE 1

| Times from respiration files | |
| --- | --- |
| T(fast scan, start) | 188.325 sec after start of file |
| T(fast scan, stop) | 193.225 sec after start of file |
| ΔT(fast scan,) | 4.9 sec |
| T(slow scan, start) | 39.725 sec after start of file |
| T(slow scan, stop) | 55.425 sec after start of file |
| ΔT(slow scan,) | 15.7 sec |

The CT acquisition computer identified each CT image with a time tag (T) and an axial position tag (z), which the inventor noted. From the time information it was possible to determine the duration of the CT scan. Values for the first and last images are shown in Table 2.

TABLE 2

| Image time stamps and z positions from CT image files. | |
| --- | --- |
| T(fast scan, image 1) | 14:21:19.24 |
| T(fast scan, image 45) | 14:21:23.31 |
| ΔT(fast scan) | 4.07 s |
| z(fast scan, image 1) | 1044.5 mm |
| | (past the ends of the lines) |
| z(fast scan, image 45) | 824.5 mm |
| | (over the phantom's motor) |
| Δz(fast scan) | −220 mm |
| T(slow scan, image 1) | 14:27:01.08 |
| T(slow scan, image 45) | 14:27:14.81 |
| ΔT(slow scan) | 13.73 |
| z(slow scan, image 1) | same as fast scan |
| z(slow scan, image 45) | same as fast scan |
| Δz(slow scan) | same as fast scan |

The inventor used this information to relate the CT scanner data to the respiratory waveform data. PHASE-MATCHING CALCULATION: The static and optimally gated (HD-Chest) PET images can be written $PET_{static}$ (x, y, z) and $PET_{og}$ (x, y, z). x, y and z represent the row, the column numbers and the image number. The phase-gated PET images had an additional index. We write $PET_{gated}$ (x, y, z, g).

In order to match PET and CT, at each position on the z axis, the gate that best matched PET to CT at each axial position z is selected. The equation EQ1 is $$PET_{matched}(x,y,z) = PET_{gated}(z,y,z,g(z)) \quad (EQ\ 1)$$

To determine g(z) we assumed that triggers were at peak inspiration, then used linear interpolation or extrapolation between the peaks. The steps were:

In the waveform file, we determined the beam on time, $T_{beam\ on}$, and beam off time, $T_{beam\ off}$, measured in seconds from the start of the file.

Using a graphical software tool, the inspiration peaks in the waveform file were identified. Since the data were from a phantom, these were spaced regularly in time. Our algorithm required only the inspiration peaks between beam-on and beam-off, and optionally one inspiration peak just before beam-on and one inspiration peak just after beam-off. This resulted in an array of values $\{T_{in\ 1}, T_{in\ 2}, \ldots, T_{in\ B}\}$ specified relative to $T_{beam-on}$ The acquisition time for each CT slice was extracted. This resulted in an array $\{T_{CT\ 1}, T_{CT\ 2}, \ldots, T_{CT\ N}\}$ where N was the number of images in the series.

For each $T_{CT\ i}$, calculate a floating-point gate value, $g_{float}(i)$ by linearly interpolating between peak times in $\{T_{in\ 1}, T_{in\ 2}, \ldots, T_{in\ B}\}$, or extrapolating if $T_{CT\ i}$ is below the first peak or above the last one. Convert this to g(z) as in (EQ 1), using the equation $$g(z)=\text{round}((g_{float}(i)-0.5)\text{modulo}\ N_{gates}) \quad (EQ\ 2)$$

Figure 10A:
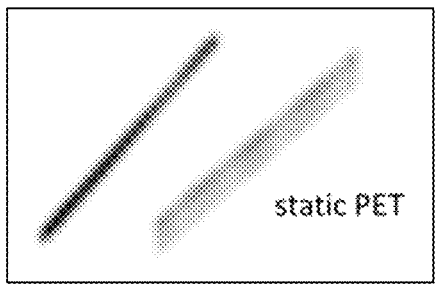
FIGS. 10A-10D show PET maximum intensity projection images (MIP) of the two-line-source phantom set up for static PET (FIG. 10A), optimally gated PET (HD Chest) (FIG. 10B), the first PET gate (FIG. 10C), and PET, matched to the low-pitch CT scan (FIG. 10D).
Figure 10B:
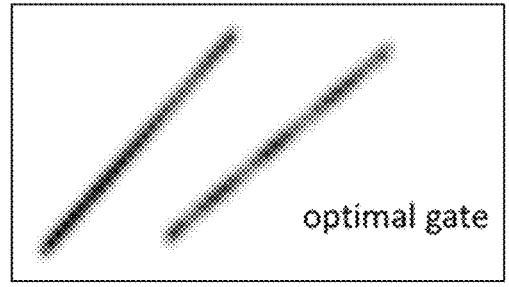
Figure 10C:
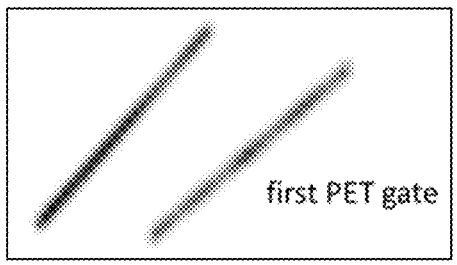
Figure 10D:
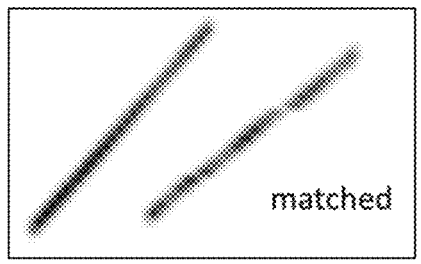
Figure 11A:
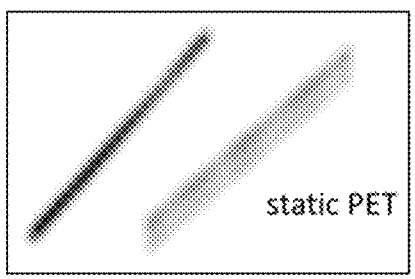
FIGS. 11A-11D show the same PET MIP images of the two-line-source phantom set up as FIGS. 10A-10D, except that in FIGS. 11A-11D, the PET MIP images are matched to the slow CT scan.
Figure 11B:
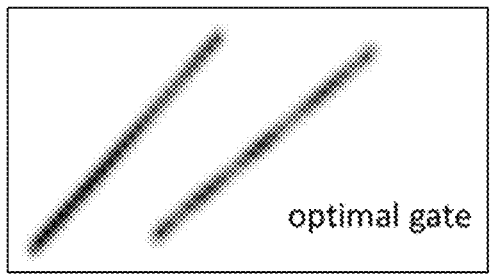
Figure 11C:
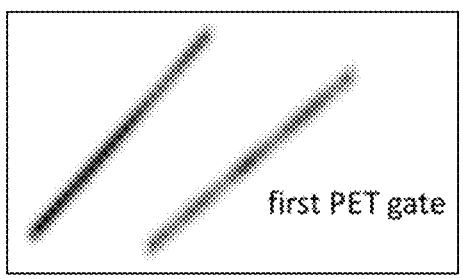
Figure 11D:
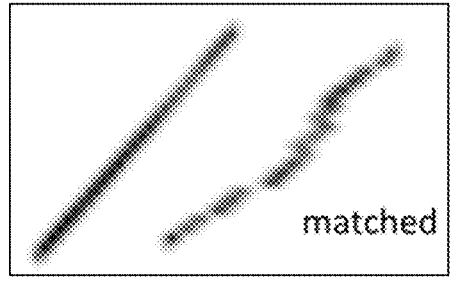
Figures 12A, 12B:
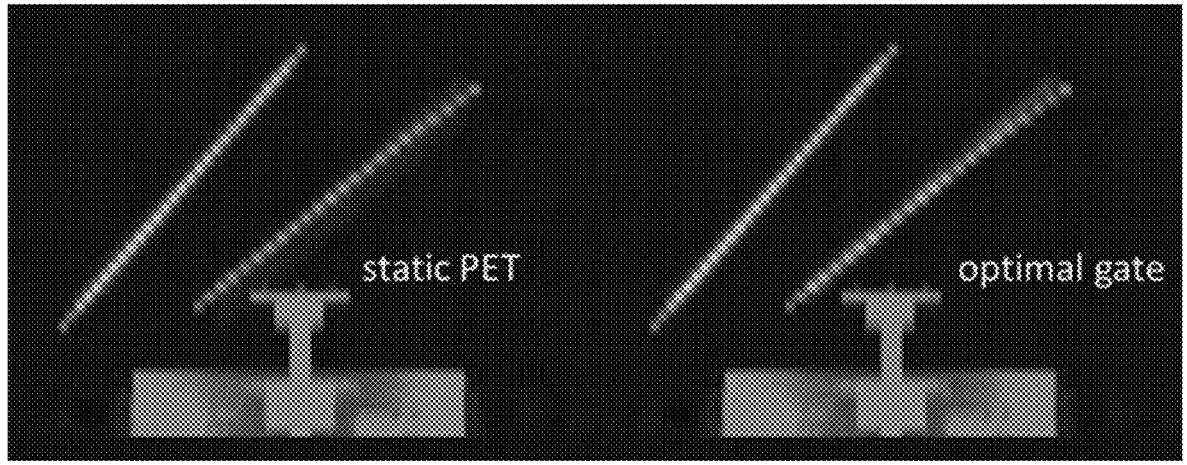
FIGS. 12A-12D show the same PET MIP images of the two-line-source phantom set up as FIGS. 10A-10D, except that in FIGS. 12A-12D, the images are fused presentation in which CT is shown by gray color and PET is shown by yellow color.
Figures 12C, 12D:
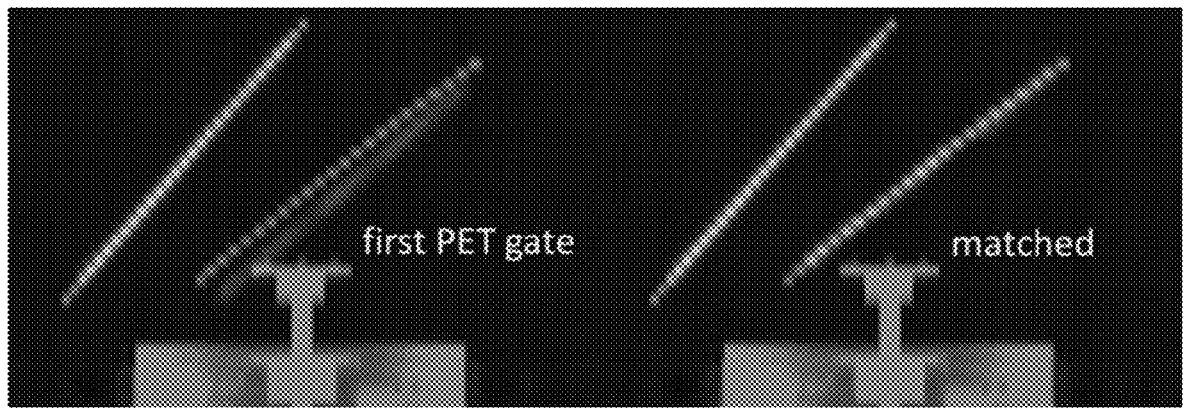
Figures 13A, 13B:
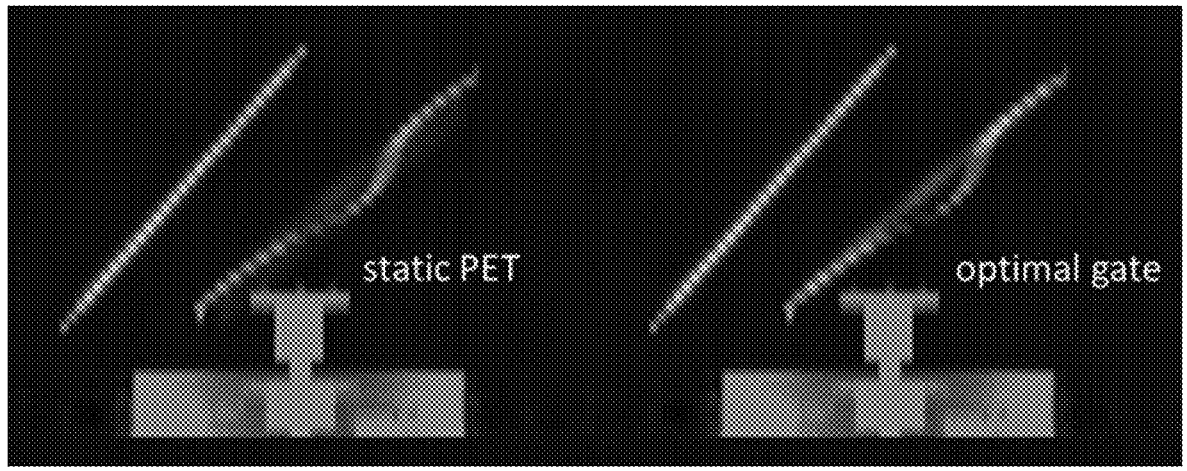
FIGS. 13A-13D show the same PET MIP images of the two-line-source phantom set up as FIGS. 11A-11D, except that in FIGS. 13A-13D, the images are fused presentation in which CT is shown by gray color and PET is shown by yellow color.
Figures 13C, 13D:
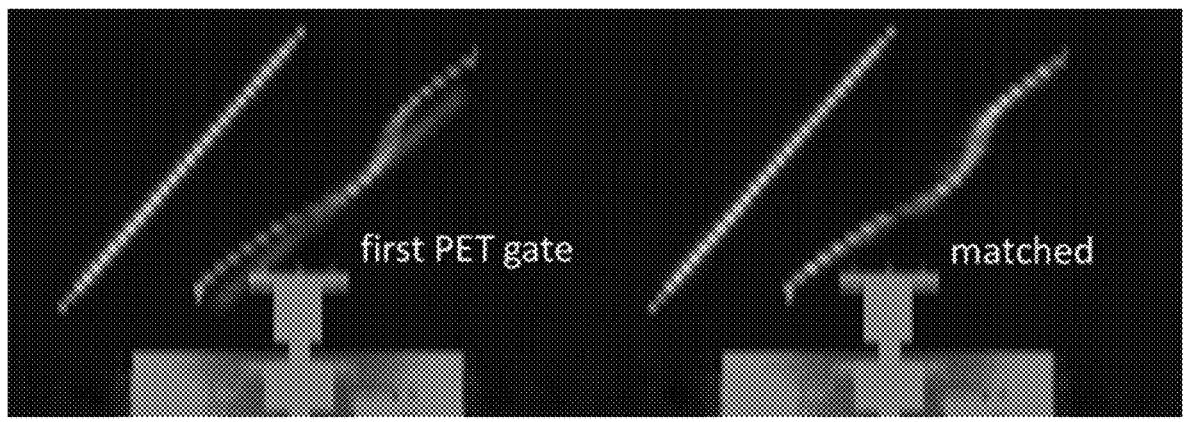

PHASE-MATCHED IMAGES: The equations 1 and 2 were applied to the moving-phantom experiment. PET-only images matched to the fast and slow CT scans are shown in FIGS. 10A-10D and 11A-11D. FIG. 10A shows a PET MIP image of the two-line-source phantom set up for static PET scan matched to the low-pitch CT scan. FIG. 10B shows a PET MIP image of the two-line-source phantom set up for optimally gated PET (HD Chest) scan matched to the low-pitch CT scan. FIG. 10C shows a PET maximum intensity projection image (MIP) of the two-line-source phantom set up for first PET gate scan matched to the low-pitch CT scan. FIG. 10D shows a PET MIP image of the two-line-source phantom set up for PET matched to the low-pitch CT scan. FIG. 11A shows a PET MIP image of the two-line-source phantom set up for static PET scan matched to the slow CT scan. FIG. 11B shows a PET MIP image of the two-line-source phantom set up for optimally gated PET (HD Chest) scan matched to the slow CT scan. FIG. 11C shows a PET MIP image of the two-line-source phantom set up for first PET gate scan matched to the slow CT scan. FIG. 11D shows a PET MIP image of the two-line-source phantom set up for PET matched to the slow CT scan.

PET's relation to CT is represented in FIGS. 12A-12D and 13A-13D by using data fusion, with CT shown in shades of gray and PET shown in shades of yellow. FIGS. 12A-12D are PET MIP images of the two-line-source phantom set up corresponding to the PET MIP images shown in FIGS. 10A-10D but in a fused presentation in which CT is shown by gray color and PET is shown by yellow color. FIGS. 13A-13D are PET MIP images of the two-line-source phantom set up corresponding to the PET MIP images shown in FIGS. 11A-11D but in a fused presentation in which CT is shown by gray color and PET is shown by yellow color.

Figure 14:
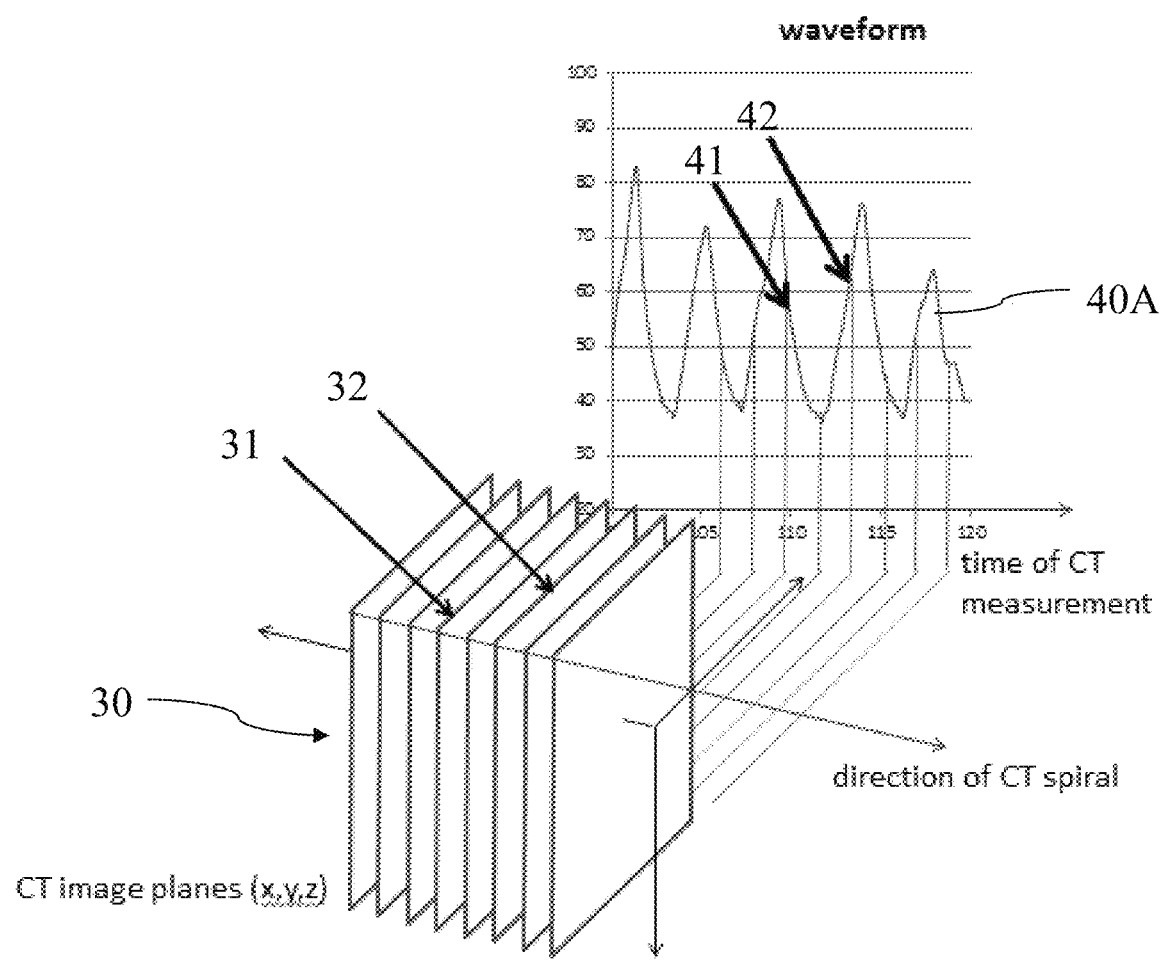
FIG. 14 is a graphical illustration of associating axial slice CT images with corresponding respiration phase on the respiratory waveform.

FIG. 14 is a graphical illustration of the method step of associating axial slice CT images 30 with corresponding respiration phases on the first respiratory waveform 40A. Each CT image plane is associated with a measurement time. This corresponds to a respiratory waveform value. For example, in FIG. 14, the particular axial slice CT images 31 and 32 correspond to the respiratory waveform values 41 and 42, respectively.

Figure 15:
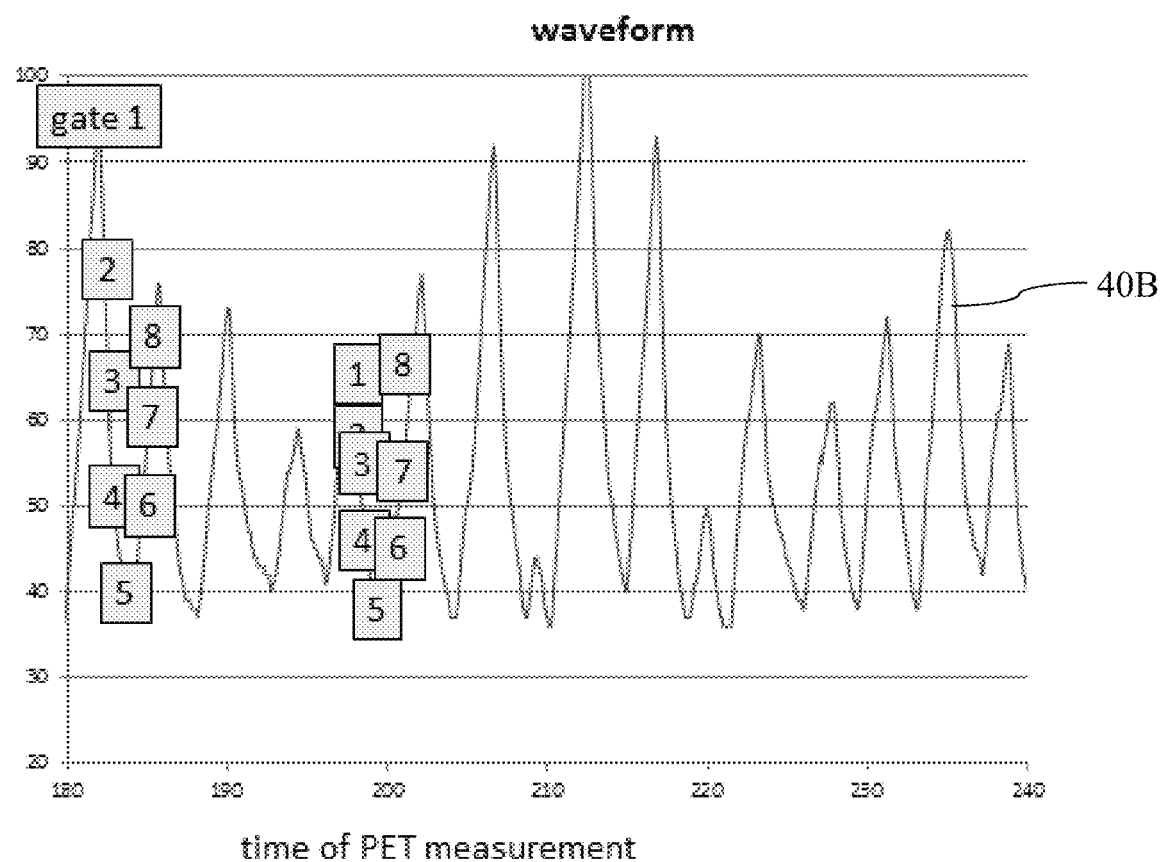
FIG. 15 is a graphical illustration of matching of each of the axial slice CT image to an emission scan image (PET image) that is associated with the same respiration phase as the corresponding CT scan-matched respiration phase.

Next, referring to FIG. 15, once all of the axial slice CT images are correlated to their respiratory waveform values, that set of data can be used to match each of the axial slice CT image with an emission scan image (PET image) that is associated with the same respiration phase as the corresponding CT scan-matched respiration phase. FIG. 15 shows the recorded respiratory waveform 40B representing the second respiratory waveform that was recorded during the emission scan of the patient. Using the plurality of CT scan-matched respiration, phases information, the respiration phases on the second respiratory waveform that matches the CT scan-matched respiration phase are identified. Then the particular emission scan images that correspond to the respiration phases on the second respiratory waveform that matches the CT scan-matched respiration phase are identified, thus, resulting in a plurality of CT image and emission image pairs that are closely matched.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A method for matching a non-gated computed tomography (CT) scan data, acquired during free breathing by a patient, to an emission scan, the method comprising the steps of:
    (a) simultaneously recording the patient's respiratory waveform and performing a non-gated CT scan of the patient, wherein the recorded respiratory waveform represents a first respiratory waveform and the non-gated CT scan generating a set of axial slice CT images, wherein recording the patient's respiratory waveform comprises receiving a trigger, determining a particular phase of the patient's respiratory waveform based on the trigger, and recording the patient's respiratory waveform based on the particular phase;
    (b) simultaneously recording the patient's respiratory waveform and performing an emission scan of the patient, wherein the recorded respiratory waveform represents a second respiratory waveform and the emission scan generating a set of emission scan images;
    (c) associating each of the axial slice CT images with a corresponding respiration phase interval or an amplitude interval on the first respiratory waveform, thus resulting in a plurality of CT scan-matched respiration phase intervals or amplitude intervals, wherein each z position in the set of axial slice CT images is uniquely associated with only the corresponding respiration phase interval or the amplitude interval; and
    (d) matching each of the axial slice CT images to an emission scan image that is associated with the same respiration phase interval or amplitude interval as the corresponding CT scan-matched respiration phase interval or amplitude interval, wherein matching each of the axial slice CT images to the emission scan image comprises:
    (e) forming gated emission sinograms (s, phi, z, theta, gate), wherein the indices s, phi, z, and theta, specify a line of response through the patient, s and phi are the position of the line of response relative to a central axis of a scanner used to perform the emission scan of the patient, z expresses a position of the line of response along the central axis, and theta is an angle the line of response forms relative to the central axis;
    (f) reconstructing the gated emission sinograms to form images (x, y, z, gate); and
    (g) at each axial slice, selecting an emission gate that matches the CT scan-matched respiration phase interval or amplitude interval acquired at position z in the CT scan, thereby forming images (x,y,z).

2. The method of claim 1, wherein the CT scan is spiral CT scan and the emission scan is positron emission tomography (PET) or single-photon emission computed tomography (SPECT).

3. The method of claim 1, wherein the step (c) comprises associating each axial slice CT image with the respiration phase interval or amplitude interval, on the first respiratory waveform, that corresponds to the position z of the axial slice CT image.

4. The method of claim 2, wherein the step (g) comprises:
identifying a plurality of respiration phase intervals or amplitude intervals on the second respiratory waveform that correspond to the plurality of CT scan-matched respiration phase intervals or amplitude intervals, thus resulting in a plurality of PET scan-matched respiration phases; and
identifying, among the set of PET scan images, those PET scan images corresponding to the plurality of PET scan-matched respiration phase intervals or amplitude intervals, thereby the PET scan images are matched to the attenuation and anatomy information in the axial slice CT images.

5. The method of claim 2, wherein the step (d) is based on:
(h) forming one PET sinogram (s, phi, z, theta) that selects PET data that matches the CT scan-matched respiration phase acquired at position z in the CT scan; and
(i) reconstructing the PET sinogram to form images (x,y,z).

6. The method of claim 5, wherein the step (h) comprises:
identifying a plurality of respiration phase intervals or amplitude intervals on the second respiratory waveform that correspond to the plurality of CT scan-matched respiration phase intervals or amplitude intervals, thus resulting in a plurality of PET scan-matched respiration phase intervals or amplitude intervals; and
identifying, among the set of PET scan images, those PET scan images corresponding to the plurality of PET scan-matched respiration phase intervals or amplitude intervals, thereby the PET scan images are matched to the attenuation and anatomy information in the axial slice CT images.

7. The method of claim 1, wherein the recording of the respiratory waveform comprises using a strain gauge or an optical tracking device.

8. The method of claim 1, wherein the recording of the respiratory waveform comprises using triggers.

9. A machine-readable storage medium, tangibly embodying a program of instructions executable by a processor to cause the processor to perform operations for matching a non-gated computed tomography (CT) scan data, acquired during free breathing by a patient, to an emission scan, the operations comprising:
(a) simultaneously recording the patient's respiratory waveform and performing a non-gated CT scan of the patient, wherein the recorded respiratory waveform represents a first respiratory waveform and the non-gated CT scan generating a set of axial slice CT images, wherein recording the patient's respiratory waveform comprises receiving a trigger, determining a particular phase of the patient's respiratory waveform based on the trigger, and recording the patient's respiratory waveform based on the particular phase;
(b) simultaneously recording the patient's respiratory waveform and performing an emission scan of the patient, wherein the recorded respiratory waveform represents a second respiratory waveform and the emission scan generating a set of emission scan images;
(c) associating each of the axial slice CT images with a corresponding respiration phase interval or an amplitude interval on the first respiratory waveform, thus resulting in a plurality of CT scan-matched respiration phase intervals or amplitude intervals, wherein each z position in the set of axial slice CT images is uniquely associated with only the corresponding respiration phase interval or the amplitude interval; and
(d) matching each of the axial slice CT images to an emission scan image that is associated with the same respiration phase interval or amplitude interval as the corresponding CT scan-matched respiration phase interval or amplitude interval, wherein matching each of the axial slice CT images to the emission scan image comprises:
(e) forming gated emission sinograms (s, phi, z, theta, gate), wherein the indices s, phi, z, and theta specify a line of response through the patient, s and phi are the position of the line of response relative to a central axis of a scanner used to perform the emission scan of the patient, z expresses a position of the line of response along the central axis, and theta is an angle the line of response forms relative to the central axis;
(f) reconstructing the gated emission sinograms to form images (x, y, z, gate); and
(g) at each axial slice, selecting an emission gate that matches the CT scan-matched respiration phase interval or amplitude interval acquired at position z in the CT scan, thereby forming images (x,y,z).

10. The storage medium of claim 9, wherein the CT scan is spiral CT scan and the emission scan is positron emission tomography (PET) or single-photon emission computed tomography (SPECT).

11. The storage medium of claim 9, wherein the step (c) comprises associating each axial slice CT image with the respiration phase interval or amplitude interval, on the first respiratory waveform, that corresponds to the position z of the axial slice CT image.

12. The storage medium of claim 10, wherein the step (g) comprises:
identifying a plurality of respiration phase intervals or amplitude intervals on the second respiratory waveform that correspond to the plurality of CT scan-matched respiration phase intervals or amplitude intervals, thus resulting in a plurality of PET scan-matched respiration phases; and
identifying, among the set of PET scan images, those PET scan images corresponding to the plurality of PET scan-matched respiration phase intervals or amplitude intervals, thereby the PET scan images are matched to the attenuation and anatomy information in the axial slice CT images.

13. The storage medium of claim 10, wherein the step (d) is based on:
(h) forming one PET sinogram (s, phi, z, theta) that selects PET data that matches the CT scan-matched respiration phase acquired at position z in the CT scan; and
(i) reconstructing the PET sinogram to form images (x,y,z).

14. The storage medium of claim 13, wherein the step (h) comprises:
identifying a plurality of respiration phase intervals or amplitude intervals on the second respiratory waveform that correspond to the plurality of CT scan-matched respiration phase intervals or amplitude intervals, thus resulting in a plurality of PET scan-matched respiration phase intervals or amplitude intervals; and identifying, among the set of PET scan images, those PET scan images corresponding to the plurality of PET scan-matched respiration phase intervals or amplitude intervals, thereby the PET scan images are matched to the attenuation and anatomy information in the axial slice CT images.

15. The storage medium of claim 9, wherein the recording of the respiratory waveform comprises using a strain gauge or an optical tracking device.

16. The storage medium of claim 9, wherein the recording of the respiratory waveform comprises using triggers.

* * * * *